United States Patent [19]
Kagan et al.

[11] Patent Number: 5,396,880
[45] Date of Patent: Mar. 14, 1995

[54] ENDOSCOPE FOR DIRECT VISUALIZATION OF THE SPINE AND EPIDURAL SPACE

[75] Inventors: Jonathan Kagan, Minneapolis, Minn.; Roger White, Memphis, Tenn.; David L. Brumfield, Nesbit, Miss.

[73] Assignee: Danek Medical, Inc., Memphis, Tenn.

[21] Appl. No.: 865,349

[22] Filed: Apr. 8, 1992

[51] Int. Cl.[6] .................... A61B 1/06; A61M 25/00
[52] U.S. Cl. ........................................... 128/6; 128/4; 128/658; 604/280
[58] Field of Search .................. 128/656, 657, 658, 4, 128/6, 7, 8, 772; 604/95, 280, 21; 385/117, 118; 606/106, 160, 164

[56] References Cited

U.S. PATENT DOCUMENTS

| | | | |
|---|---|---|---|
| 3,332,425 | 7/1967 | Luborsky et al. | 606/106 |
| 4,245,624 | 1/1981 | Komiya | 128/4 |
| 4,659,195 | 4/1987 | D'Amelio et al. | 128/4 X |
| 4,770,653 | 9/1988 | Shturman | 604/21 |
| 4,838,879 | 6/1989 | Tanabe et al. | 128/658 X |
| 4,899,732 | 2/1990 | Cohen | 128/6 |
| 4,900,122 | 2/1990 | Frank et al. | 385/117 X |
| 4,988,356 | 1/1991 | Crittenden et al. | 128/657 X |
| 5,030,204 | 7/1991 | Badger et al. | 128/657 |
| 5,117,839 | 6/1992 | Dance | 128/772 |
| 5,125,896 | 6/1992 | Hojeibane | 604/95 |
| 5,152,277 | 10/1992 | Honda et al. | 128/4 |
| 5,161,534 | 11/1992 | Berthiaume | 128/657 |
| 5,163,911 | 11/1992 | Sirimanne et al. | 128/772 |

Primary Examiner—Richard J. Apley
Assistant Examiner—John P. Leubecker
Attorney, Agent, or Firm—Woodard, Emhardt, Naughton, Moriarty & McNett

[57] ABSTRACT

A system for direct visualization of the spine and the epidural and/or intra-discal space to facilitate diagnosis and treatment of spinal conditions and that is adapted for percutaneous introduction into the spinal space. The system includes a disposable flexible catheter, a fiber-optic bundle disposed within the catheter which is connected to a light source and camera. The bundle is removably and adjustably connected to the proximal end of the catheter to permit rotation of the bundle relative to the catheter. A mechanism for controllably deflecting the tip of the catheter is provided to vary the viewing angle of the fiber-optic bundle within and to assist in steering the catheter through the spinal space. The mechanism includes a deflection wire extending through the catheter and affixed at the distal end thereof. The proximal end of the deflection wire is affixed to a sleeve which is slidably disposed around the catheter and within a housing. The housing includes an internal flange that defines a stop surface which is contacted by the sleeve as the catheter and deflection wire is moved in a first direction. After the sleeve contacts the stop surface, further movement of the catheter in the first direction causes tension in the wire between the sleeve and the wire's securement to the catheter, thereby bending the catheter tip in the direction of the securement. The catheter can be rotated with the tip in its deflected position to provide a conical viewing region within the spinal space.

38 Claims, 4 Drawing Sheets

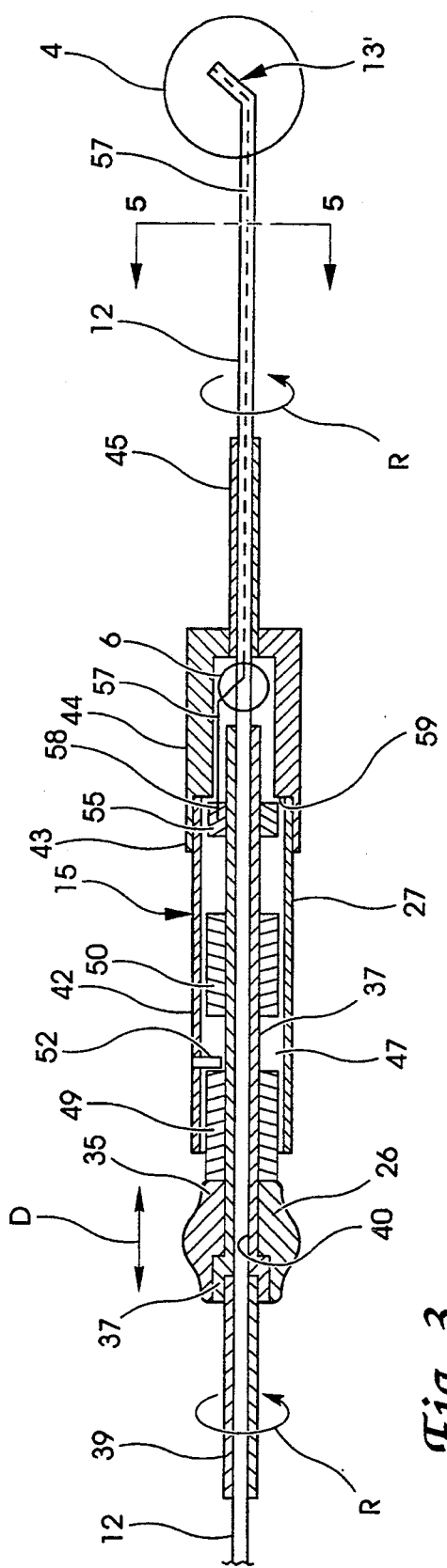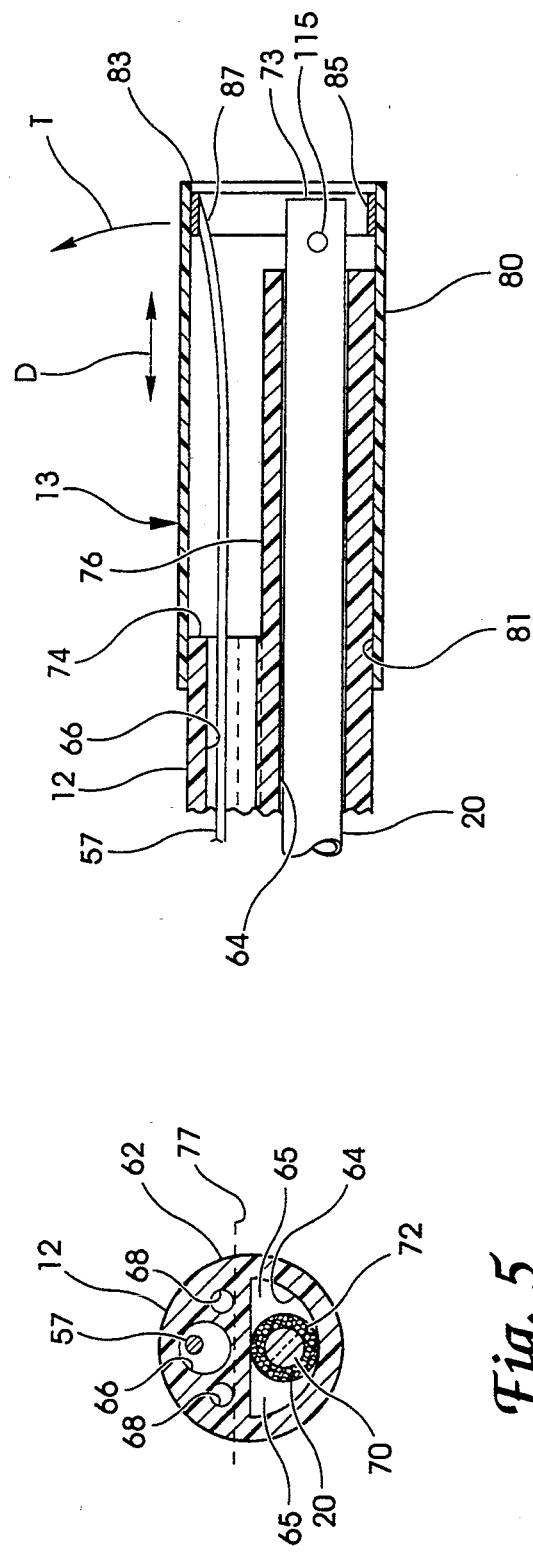

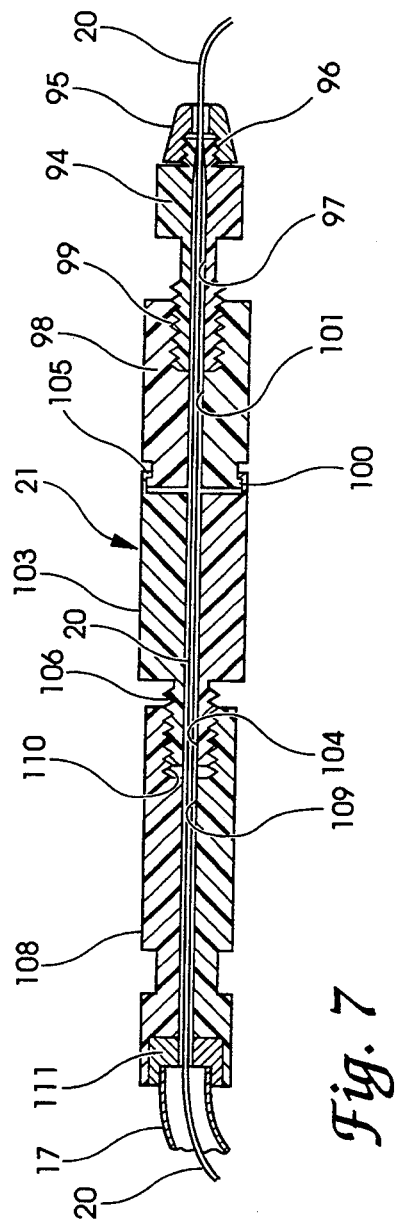
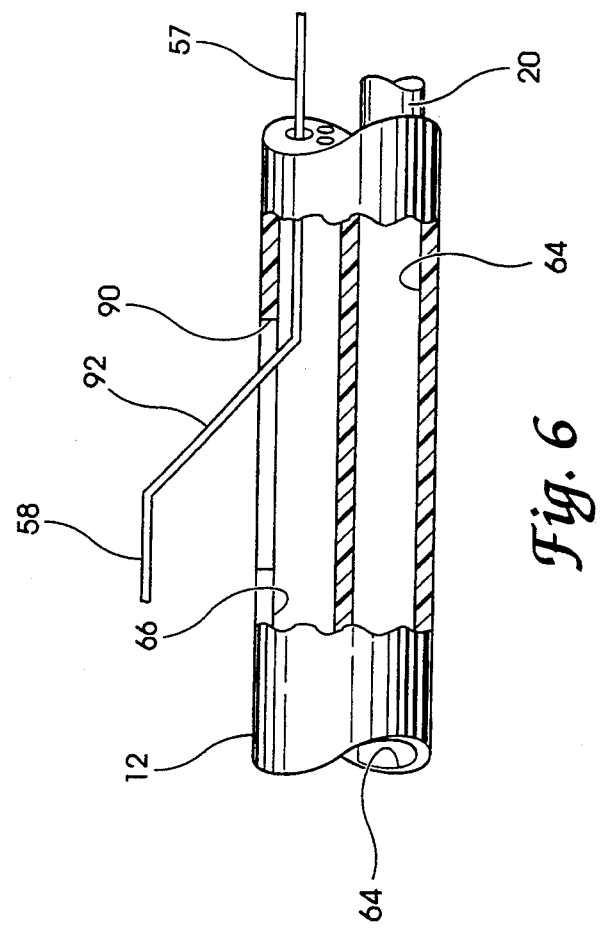

ENDOSCOPE FOR DIRECT VISUALIZATION OF THE SPINE AND EPIDURAL SPACE

BACKGROUND OF THE INVENTION

This invention relates to a device for use hi visualization of the spine in vivo for diagnosis and treatment. More particularly, the invention concerns a flexible endoscope having a deflecting tip for changing the viewing angle of a removable fiber-optic bundle and for providing a means for steering the endoscope through tight spaces.

Low back pain syndrome represents a major health problem in the United States. In recent years, practitioners in the spinal field have sought methods to minimize the invasive nature of diagnosis and treatment of the causes of low back pain syndrome. Surgeons and other practitioners in the field have also sought ways to minimize the invasive nature of other more serious spinal surgery such as reducing vertebral fractures, implanting prosthetic vertebrae or implanting spinal fixation devices.

Typically, spinal diagnosis and treatment is conducted under indirect visualization techniques, such as magnetic resonance imaging (MRI), catscan (CT) and more frequently, fluoroscopic X-ray or radiographic monitoring using a C-arm image intensifier. Direct visualization of specific affected regions of the spine can be obtained through surgical incisions through the skin and fat layer. Less invasive percutaneous techniques, such as suggested by Jacobsen in U.S. Pat. No. 4,545,374 or by Kambin in U.S. Pat. No. 4,573,448, are thus far typically performed under indirect visualization. There remains a need therefore, for a means for direct visualization of the spinal column, including the vertebrae, disc tissue and the epidural and intra-discal spaces, without extensive surgery.

Visualization of the spine carries with it significant difficulties over visualization of other body regions, such as the knee. Direct visualization of the knee has been readily accomplished using rigid arthroscopes, since there is very little requirement for guiding or steering the fiber-optic bundle through this joint. On the other hand, the spinal column consists of several joints. Moreover, the configuration of the vertebrae themselves hamper the ability for direct visualization, at least using a rigid endoscope device. Oftentimes, it is necessary to view a vertebra from both posterior and anterior positions. No known rigid endoscope appears to be capable of permitting direct visualization in all regions of the spinal column.

Consequently, there is a significant need in the field of spinal diagnosis and treatment for a device that permits direct visualization of the spine in vivo from virtually any position. The device must be flexible so that it can be guided to the different positions along the spine. It must also have the capability of changing the orientation of the viewing angle field as required to fully visualize the suspect region of the spine.

BRIEF DESCRIPTION OF THE DRAWINGS

FIG. 3 is a side cross-sectional view of the tip deflection mechanism used in connection with the endoscopic device of FIG. 2.

FIG. 4 is an enlarged view of the deflecting tip of the catheter for the endoscope shown in FIG. 3, as viewed in the region labeled 4 of that figure.

FIG. 5 is an end cross-sectional view of the introducer catheter used in connection with the endoscopic device shown in FIG. 3 taken along line 5—5 as viewed in the direction of the arrows.

FIG. 6 is an enlarged view of the introduction of the deflection wire into the introducer catheter, as shown in the detail region labeled 6 in FIG. 3.

FIG. 7 is a side cross-sectional view of the optical fiber adjustment means shown in FIG. 2 for adjusting the position of the fiber-optic bundle with respect to the introducer catheter.

SUMMARY OF THE INVENTION

Figure 1:
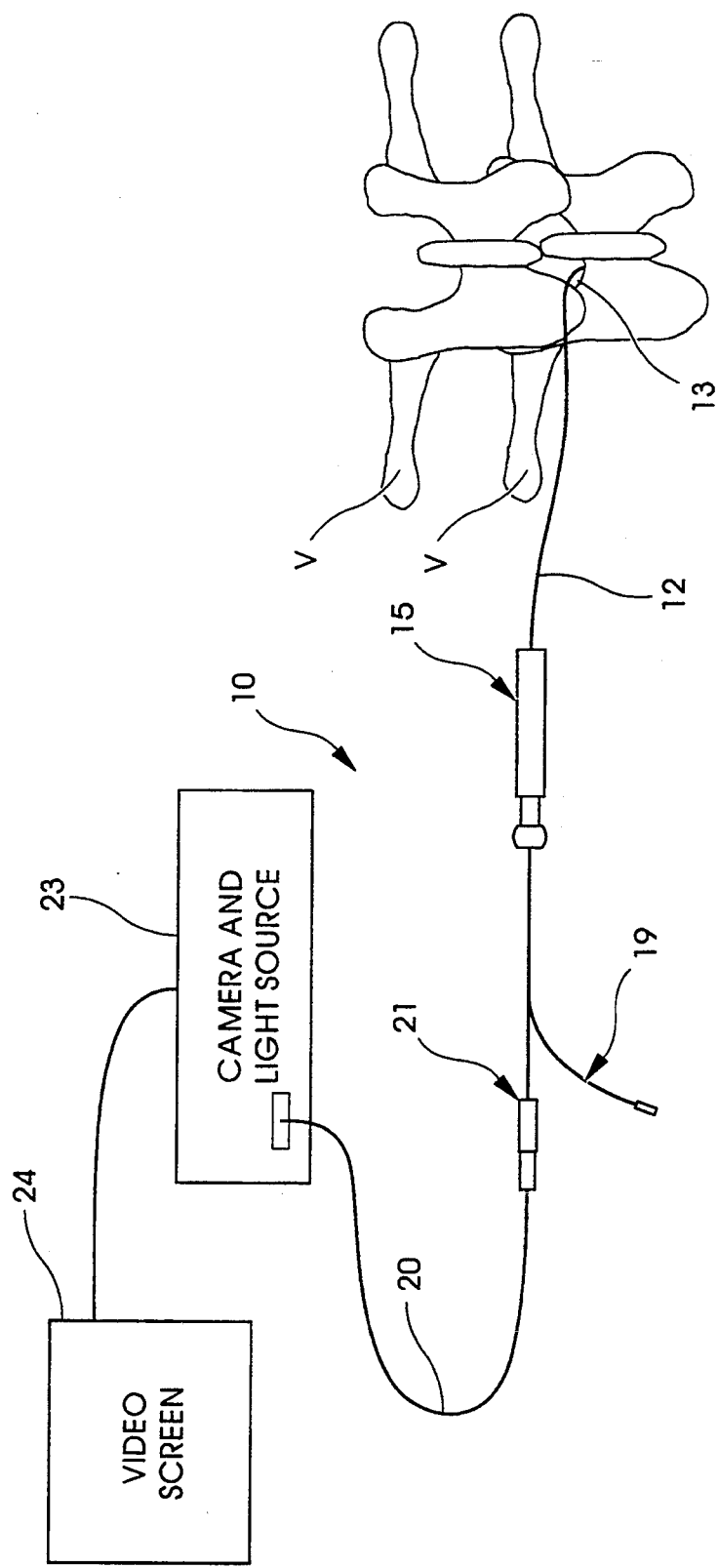
FIG. 1 is a schematic representation of the endoscopic device for direct spinal visualization of the present invention.

The present invention contemplates a system for direct visualization of the spine and epidural space that is adapted for percutaneous introduction into the epidural and/or intra-discal spaces. In general terms, the system includes a disposable flexible catheter, a fiber-optic bundle disposed within the catheter, means for connecting the bundle to a light source and camera, means for adjustably connecting the bundle to the proximal end of the catheter, and means for controllably deflecting the tip of the catheter to vary the viewing angle of the fiber-optic bundle in the spinal space. Deflection of the viewing tip also provides means for controllably steering the catheter through tight regions in the spinal space.

More particularly, the inventive system includes a small diameter disposable flexible catheter having a first channel extending along the entire length of the catheter opening at the distal end of the catheter at a deflectable or bendable tip. A fiber-optic bundle, which includes coaxially disposed imaging fibers and light fibers, is slidably received within the first channel. Means are provided for engaging the imaging fibers to a camera and the light fibers to a light source. In one embodiment, the first channel also serves as an irrigation channel in addition to supporting the fiber-optic bundle. Means are also provided for fluidly engaging the first channel to a source of irrigation fluid.

Means are provided at the proximal end of the catheter for connecting the fiber-optic bundle to the proximal end of the catheter and for adjustably positioning the distal end of the bundle relative to the distal end of the catheter. In one aspect, this connecting means includes a clamp for clamping the fiber-optic bundle and means for adjusting the length distance between the distal end of the catheter and the clamp means. More particularly, the connecting means contemplates a first housing attached to the proximal end of the catheter and a second housing connected to the clamp. A bore passes through both housings for slidably receiving the fiber-optic bundle therethrough. A threaded post on the second housing and a mating threaded bore in the first housing are adjustably threaded together to adjust the length distance between the distal end of the catheter and the clamp. As the post is threaded into the bore, the two housings move closer together thereby reducing the distance between the catheter distal end and the clamp for the fiber-optic bundle. Thus, the viewing end of the bundle moves toward the end of the catheter. On the other hand, unthreading the post from the bore increases the distance between catheter distal end and clamp, thereby causing the fiber-optic bundle to, in effect, recede within the catheter. Radio-opaque markings can be made at the distal ends of the catheter and the fiber-optic bundle to permit radiographic verification of the relative position of the distal end of the bundle to the distal end of the catheter.

In a further feature of the connecting means, means are also provided for rotating the fiber-optic bundle relative to the catheter. This rotation means includes a third housing attached to the clamp which is rotatably mounted on the second housing to permit relative rotation between the housings.

As expressed generally above, the system also includes means for controllably deflecting the tip of the catheter when the distal end is in the epidural space. This tip deflection means includes a deflection wire having a first end and a second end in which a first portion of the wire is adjacent the first end disposed outside the catheter and a second portion of the wire between the first portion and the second end extends through the catheter. The second end of the deflection wire is secured to the catheter at the distal end. In one particular aspect, the wire is affixed to a stainless steel ring which is affixed to the end opening of a tube mounted at the tip of the catheter.

The tip deflection means further includes means for moving the catheter in a first direction oriented toward the distal end of the catheter and means for restraining the first end or the deflection wire against movement in the first direction as the catheter is moved in that direction. In one embodiment, the means for restraining the deflection wire includes an elongated housing defining a cavity therein, the housing having openings at its ends for slidably receiving the catheter therethrough. The first end of the deflection wire is connected to a sleeve within the cavity which is slidably disposed about the catheter. The housing includes a flange in the cavity which is a stop surface for restraining movement or the sleeve in the first direction. In the operation of the tip deflecting means, movement of the catheter in the first direction carries the deflection wire until the sleeve contacts the stop surface of the flange. As the catheter is moved further in the first direction, the wire is put into tension between the restrained first end and the second end affixed to the catheter distal end. This tension operates to pull the portion of the catheter back to which the deflection wire is attached, thereby bending the catheter tip in the direction of the attachment of the deflection wire.

In a further aspect of the invention, the means for moving the catheter includes means for limiting movement of the catheter in the first direction relative to the deflection wire sleeve once the sleeve has contacted the stop surface. Limiting the catheter movement in the first direction controls or limits the amount of deflection of the tip. This means for limiting movement can include a first stop connected to the catheter which is slidable within the cavity and a pin affixed to the housing and projecting into the cavity between the first stop and the sleeve. Thus, the first stop will contact the pin when the catheter is moved in the first direction. The first stop is situated at a predetermined distance from the pin when the sleeve contacts the flange stop surface such that movement of the catheter and the first stop through the predetermined distance will result in a controlled tip deflection, which can range from 0° to about 90°. A second stop may also be included which is connected to the catheter and slidable within the cavity between the pin and the sleeve, whereby the second stop contacts the pin when the catheter is moved in a second direction opposite the first direction. The means for moving the catheter also includes means for rotating the catheter with the tip deflected so the fiber-optic bundle can be swept through a conical viewing field within the epidural space.

One aspect of the invention resides in the construction of the catheter itself. The catheter can include a send-circular first channel through which the fiber-optic bundle extends. The diameter of the bundle can be slightly less than the radius of the semi-circular channel to support the bundle without excessive movement. A second channel can also be provided for receiving the deflection wire. The second channel includes a slot opening into the second channel through which the deflection wire extends. In one feature, the second channel terminates short of the distal end of the catheter and the catheter has a reduced outer dimension from the end of the second channel to the distal end of the catheter. The deflection wire then projects from the end of the second channel adjacent the reduced outer dimension to its securement on the outer tube. Optionally, a third channel may be provided for introduction of working instruments or a laser fiber.

The invention also contemplates a method for direct visualization of the spine and epidural space. The method uses an endoscope formed of a flexible catheter with a fiber-optic bundle slidably disposed therein, catheter having a deflectable tip and the fiber-optic bundle being connected to a light source and camera. In one step of the method, the catheter is percutaneously inserted into the body and placed within the epidural space in a region to be observed. The fiber-optic bundle is kept retracted within the catheter until the catheter tip reaches the region. The fiber-optic bundle is then extended relative to the catheter until the viewing end of the bundle is adjacent the end of the catheter, which position is radiographically verified.

The method further contemplates steps of deflecting the catheter tip to vary the viewing angle of the viewing end of the fiber-optic bundle within the epidural space, rotating the catheter with the tip deflected, and rotating the fiber-optic bundle relative to the catheter, all in order to vary the viewing angle and view orientation of the image transmitted through the fiber-optic bundle. Each of these steps may occur relatively simultaneously or in sequence as required to provide full visualization of the epidural space.

It is one object of the invention to provide a system for direct visualization of the spine and epidural space. Another object is achieved by providing an endoscope formed by a disposable flexible catheter through which a fiber-optic bundle extends. The catheter is adapted to accommodate a fiber-optic bundle that is either reusable or disposable.

A further object contemplates an endoscope for direct spinal visualization which has a small diameter for percutaneous insertion, yet still includes the capability to vary the viewing field within the epidural space. This object is achieved by the catheter including means for deflecting the tip with the fiber-optic bundle within, as well as for rotating the catheter with the tip deflected and rotating the fiber-optic bundle relative to the catheter.

A further object is to provide these features for varying the viewing field in a device that includes few moving parts and that is easily assembled. Optionally, all of the components providing these features can be disposable.

Further objects, along with certain benefits achieved by this invention, will become apparent to persons of ordinary skill in the art, upon consideration of the following written description and accompanying figures.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring first to FIG. 1, the spinal visualization system 10 of the present invention is depicted. In particular, the visualization system 10 is an endoscopic system which includes a delivery catheter 12 having a deflecting viewing tip 13. As shown in FIG. 1, the catheter can be introduced into the body using a separate introducer cannula set known in the art. The delivery catheter 12 can be introduced with the deflecting tip 13 adjacent the spinal column or specific vertebra of the spine. The delivery catheter 12 and tip 13 constitute an endoscope for direct vision of the spine. A hand piece 15 is provided for deflecting the tip and for rotating the viewing tip 13 to provide a full viewing field of the spine.

Irrigation port means 19 is included to provide irrigation to the delivery catheter 12. Irrigation fluid can be introduced through the tip 13 into the spinal region to clear obstructions in the viewing field. A fiber-optic bundle 20 passes through the delivery catheter 12 to form the vision component of the flexible endoscope. An optic bundle adjustment means 21 is provided which orients the viewing tip of the fiber-optic bundle 20 with respect to the deflecting tip 13 of the delivery catheter. The proximal end of the fiber-optic bundle 20 is engaged in a conventional manner to a camera and light source 23 which can be of known construction. A video screen 24 connected to the camera 23 televises the images of the spine for direct viewing by medical personnel. In accordance with the present invention, the video screen 24, camera and light source 23 and fiber-optic bundle 20 can be of a known commercially available design. For example, the camera and light source can be the Model 2000 system provided by Citation Medical Co. The fiber-optic bundle can be custom configured using known technology to account for the need of specific applications of the system.

In use, the delivery catheter 12 can be inserted percutaneously into the patient using a cannula, trocar or similar instrument. The flexible nature of the catheter allows the viewing tip to be guided through or around the vertebrae to the affected region. The viewing tip 13 can then be orient for a better view or it can be manipulated throughout the region.

As will be described herein, the construction of the visualization system 10, and particularly the delivery catheter 12, permits potential reuse of the fiber-optic bundle 20 which can be easily and readily inserted into the catheter to a proper viewing position. Alternatively, the bundle 20 may itself be disposable and provided together with the catheter in disposable sterile packaging.

Figure 2:
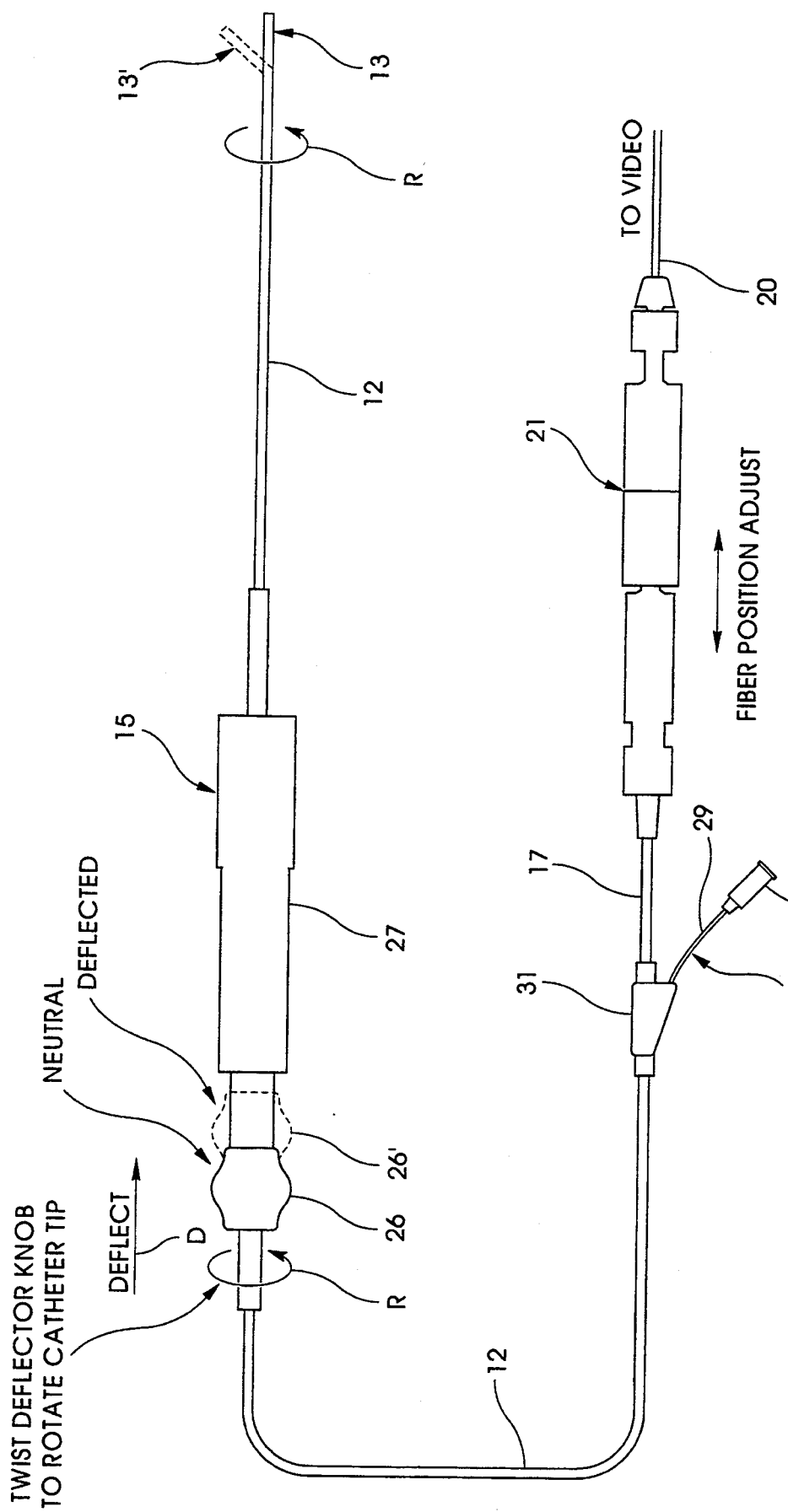
FIG. 2 is an enlarged view of the endoscopic device of FIG. 1.

Referring now to FIG. 2, more detail of the visualization system 10 is shown. In particular, the delivery catheter 12 is shown with the viewing tip 13 also shown in its deflected position 13' which is oriented at an angle of approximately 45° to the undeflected position of the tip (at least in one specific embodiment). The hand piece 15 includes a plunger 26 which operates within a deflection control mechanism 27. The plunger 26 can be depressed in the direction of the arrow D to a second position 26' which corresponds to the deflected position 13' of the viewing tip. The plunger 26 can also be rotated in the direction of the circular arrow R to thereby rotate the delivery catheter 12 and viewing tip 13 in a similar direction. Thus, the handpiece 15 provides for a wide viewing field with the fiber-optic bundle contained within the delivery catheter 12. In one specific embodiment of the invention, depicted in FIGS. 2 and 3, the illustrated tip deflection permits the viewing tip 13 to be swept through a cone angle of about 45°. It is understood, or course, that this specific embodiment is not intended to limit the tip deflection capability of the present invention. More specifically, the hand piece 15 can be configured to produce viewing tip deflections or cone angles which can vary between 0° and about 90°.

As shown in FIG. 2, the delivery catheter 12 extends through the hand piece 15 to engage a tubing junction 31. The tubing junction 31 forms part of the irrigation port means 19. An irrigation tube 29, which preferable terminates at its proximal end in a Luer Loc ® connection 30, can be integral with the tubing junction 31. A second catheter tube 17 is also connected to the junction 31. The second catheter tube 17 is attached to the fiber-optic adjustment means 21 and accommodates the fiber-optic bundle 20 passing therethrough. Thus, the tubing junction 31 marries tube 17 initially carrying the fiber-optic bundle 20 to a means for providing irrigation fluid 19 which combine to pass both irrigation fluid and fiber-optic bundle through the catheter 12 to the viewing tip 13.

The details of the band piece 15 are shown more clearly in the cross-sectional view of FIG. 3. In particular, the hand piece 15 includes the plunger 26 which comprises a plunger handle 35 and a stiffening sheath 37 affixed to and supported by the handle 35. A guide tube 39 projects from the forward end of the plunger handle 35. The stiffening sheath 37 and guide tube 39 define a bore 40 through which the flexible delivery catheter 12 is inserted. The stiffening sheath 37 projects distally from the plunger handle 35 and the bore 40 is sized so that a very close fit is provided around the catheter 12. The catheter is fixed to the stiffening sheath 37 or guide tube 39, such as by epoxy or welding, so that the catheter 12 moves with the plunger handle 35.

The stiffening sheath 37 supports the catheter 12 as it projects into a housing 42 and an end housing 44. The two housings are mated at joint 43 to define a cavity 47 with the plunger 35 situated at the open end. A guide tube 45 projects from the distal end of the end housing 44 to provide additional guidance and support to the delivery catheter 12 as it exits both the stiffening sheath 37 and the end housing 44.

A left stop 49 and a right stop 50 can be affixed to the outer diameter of the stiffening sheath 37, in one specific embodiment. In an alternative embodiment, the plunger handle 35, stiffening sheath 37 and stops 49 and 50 can be integrally formed into a single piece. A pin 52 is affixed to the housing 42 to project into the cavity 47 between the stop 49 and stop 50. The pin 52 thus limits the movement of the plunger 26 in the direction of the arrows D. Thus, pin 52 helps to keep the hand piece assembly 15 together as well as to limit the amount of deflection of the viewing tip 13.

Slidably disposed between the housing 42 and the stiffening sheath 37 is a deflection control sleeve 55. The deflection wire 57 is affixed to the control sleeve 55 at a proximal attachment portion 58 of the wire. Preferably, the attachment portion 58 of wire 57 is embedded in the control sleeve 55, although other means of affixing the proximal end of the wire to the sleeve is contemplated. The deflection wire 57 extends through the remaining length of the catheter 12 and its distal end is fastened to the catheter at the viewing tip 13 in a manner to be discussed herein. A flange 59 is provided in the end housing 44 to act as a stop surface for movement of the control sleeve 55 in the direction D.

In the operation of the hand piece assembly 15, deflection of the tip 13 is accomplished by way of the relative movement of the catheter 12 with respect to the deflection wire 57. More specifically, as the plunger 26 is depressed into the cavity 47 of housing 42, the catheter 12, which is fixed to the plunger, also moves and extends further beyond end housing 44. As the catheter 12 moves, the deflection wire 57, which is affixed to the tip 13 of the catheter, also moves until the control sleeve 55 contacts the flange 59. At this point, further movement of the catheter 12 relative to the now restrained deflection wire 57 creates tension in the deflection wire which tries to pull the tip 13 back as the catheter 12 continues to advance. The tip 13 will continue to bend until the left stop 49 contacts the pin 52 at which point the tip as at its maximum deflected position 13'. It is understood that once the control sleeve 55 contacts the flange 59, the deflection wire 57 will no longer translate. Instead, the tension in the deflection wire 57 will cause the wire to pull the tip 13 back toward the control sleeve 55.

The tip can be returned from its deflected position 13' to its undeflected position by pulling the plunger 35 back in the opposite direction, which gradually decreases the tension in the deflection wire 55. The natural resilience of the catheter material, as well as the resilience of the deflection wire, will then cause the catheter to straighten. This same resilience may tend to cause the catheter to straighten without pulling back on plunger 35. Moreover, the plunger 35 may be biased to the neutral undeflected tip position by way of a spring situated, for example, between the right stop 50 and the flange 59.

As previously explained, rotation of the tip 13 can be achieved by rotating plunger 35 in the direction of arrow R. The deflection wire 57 also rotates with the tip so simultaneous deflection and rotation of the tip is permitted. The control sleeve 55 will also rotate as it is pulled by the deflection wire. The control sleeve 55 and sheath 37 may include mating radial splines (not shown) so rotation of the plunger is directly transmitted to the control sleeve.

Referring next to FIG. 4, the engagement of the deflection wire 57 to the tip 13 is shown in more detail. Specifically, the tip 13 includes an outer end tube 80 which is affixed to the delivery catheter at joint 81. The end tube 80 has an open end 83 to provide an opening for viewing through the fiber-optic bundle 20. A stainless steel ring 85 is engaged within the end tube 80, preferably immediately adjacent the open end 83. The ring 85 can either be epoxied to the tube or the tube 80 can be shrunk onto the ring to hold it firmly in position. The deflection wire 57 is then fixed to the ring 85 at a fixation point 87, preferably at the top of the ring, by welding or other fixation. It can thus be seen that as the catheter 12 and tip 13 move in the direction of the arrows D, and particularly to the right as shown in FIG. 4, the deflection wire 57 tries to maintain its same length and consequently pulls the tip 13 back toward the hand piece assembly 15 as the catheter 12 is pushed to the right.

The present invention contemplates a completely disposable catheter arrangement for use with either a reusable or no-reusable disposable fiber-optic bundle 20. The construction of the delivery catheter 12 is shown in the cross-sectional view of FIG. 5. The catheter includes a body 62 which is preferably made of standard grade medical plastic, such as polyurethane, extruded into the appropriate configuration. The body in one specific embodiment has an outer diameter of 2.0–2.75 mm to facilitate movement in the tight quarters of the epidural space and to keep the puncture site diameter as small as possible. However, the present invention contemplates a smaller catheter diameter, about 1.0 mm, with the catheter features (such as channel dimensions) being correspondingly reduced in size. The length of the catheter 12 from tip 13 to tubing junction 31 is about 840.0 mm (33 inches).

The body defines an irrigation channel 64 which is preferably semi-circular in shape and occupies the lower half of the circular body 62. Disposed within the irrigation channel 64 is the fiber-optic bundle 20. The diameter of the fiber-optic bundle is slightly smaller than the lumen of the semi-circular irrigation channel 64 which in one specific embodiment is 0.89–1.35 mm (corresponding to a catheter outer diameter of 2.0–2.75 mm). Thus, the bundle can be loosely fed into the catheter 12 through the irrigation channel 64 and remain in this position. The space 65 around the fiber-optic bundle 20 in the irrigation channel 64 can be used for flowing irrigation fluid through the catheter to the viewing site.

As can be seen in FIG. 5, the fiber-optic bundle 20 of one specific embodiment includes an image bundle 70 surrounded by a number of light fiber bundles 72. The fiber-optic bundle 20 can be surrounded by a sheath as required to avoid damage to the fiber-optic components. Other fiber-optic bundle configurations are contemplated, however, the diameter of the bundle preferably has an outer diameter of 0.8–1.2 mm. The image bundle 70 preferably has an outer diameter of between 0.35 and 0.5 mm and a resolution of 6,000–12,000 pixels.

The catheter body also includes a guide wire channel 66 through which the guide wire 57 extends. In one specific embodiment, the guide wire channel 57 has a diameter of 0.58–0.76 mm (corresponding to a catheter outer diameter of 2.0–2.75 mm). A pair of stiffener channels 68 are also provided in the catheter body 62. A pair of stiffening rods (not shown) can be readily inserted through the channel 68 to add rigidity to the delivery catheter 12. The stiffener channels can terminate short of the distal end of the catheter so that unnecessary stiffness is not added at the deflecting tip. In lieu of separate stiffeners, the deflection wire 57 itself can include a stiffening sheath around the wire.

Referring again to FIG. 4, it can be seen that the catheter body 62 includes a cut-back 74 at the deflection wire channel half of the body. More particularly, a truncated outer wall 76 surrounding the irrigation channel 64 is provided by longitudinally slicing the catheter body 62 at a cut line 77 shown in FIG. 5. The catheter body is cut back from the open end 83 of the outer end tubing 80 to the cut-back portion 74 to leave the guide wire 57 exposed. This cut-back portion, or more particularly the length of the truncated outer wall 76, corresponds generally to the length of the tip that will be deflected upon actuation of the hand piece assembly 15. The tip length is preferably between 1.0–2.5 cm. In one specific embodiment, this tip length is 1 cm. As can also be seen in FIG. 4, the viewing end 73 of the fiber-optic bundle 20 is disposed just inside the open end 83 of the outer end tubing 80. The viewing end 73 is preferably shielded in this manner so that it does not contact the body tissue as the catheter is introduced into the spinal region.

Referring now to FIG. 6, the manner in which the deflection wire 57 is disposed into the catheter 12 is illustrated. As shown in this figure, the deflection wire channel 66 includes a slot 90 through the outer wall of the catheter body 62. The deflection wire 57 then passes through that slot into the deflection wire channel 66. More specifically, the deflection wire 57 include a clearance bend 92 which allows the wire 57 to clear not only the catheter body 62 but also the stiffening sheath 37 (FIG. 3). The attached portion 58 of the wire extends from the clearance bend 92 and is affixed to the control sleeve 55 as previously discussed. The slot 90 is long enough to permit the catheter to translate relative to the clearance bend 92 for the full deflection capability of the viewing tip 13, without the deflection wire 57 contacting the ends of the slot 90. The slot 90 can be narrow so that rotation of the catheter 12 due to rotation of the plunger 35 reacts to push the wire, and hence the control sleeve 55, in the direction of rotation.

Since the present invention contemplates a fiber-optic bundle 20 separate and independent of the disposable delivery catheter 12, an optical bundle adjustment means 21 is provided. The bundle 20 is preferably threaded through the adjustment means 21, tube 17, junction 31 and into irrigation channel 64 of catheter 12 until it is at the viewing tip 13. The adjustment means 21 allows the operator to vary the position of the viewing end 73 of the bundle 20 with respect to the open end 83 of the outer end tubing 80 at the tip 13. As the catheter 12 is conveyed into the spinal site, the bundle is preferably pulled back front the tip while irrigation fluid is used to keep the catheter clear of tissue. Once at the spinal site, the bundle 20 and particularly viewing end 73 should be close to the open end 83 for optimum viewing. During a visualization procedure, manipulation of the fiber-optic bundle 20 may be required to keep the viewing end disposed within the outer end tubing 80, or to provide a more optimum position for the viewing end for a wider field of vision. In addition, it is often necessary to rotate the fiber-optic bundle to thereby rotate the image transmitted by the imaging bundle 70. These functions are provided by the adjustment means 21.

The optic bundle adjustment means 21 includes a locking base 94 and a conical locking nut 95. The locking nut 95 is threaded onto a threaded post 96. A bore 97 is defined by the base 94 and threaded post 96 through which fiber-optic bundle 20 extends. The threaded post 96 is preferably resilient or is slotted so that it can be compressed onto the outer surface of the optic bundle 20 to grip the bundle. As the conical locking nut 95 is threaded onto the post, it forces the walls of the post to trap the fiber-optic bundle 20.

A rotator body 98 is also provided to which the locking base 94 is fixed, such as by a threaded connection 99. The rotator body 98 includes a swivel flange 100 and a bore 101 extending therethrough. Naturally, the fiber-optic bundle 20 extends through this bore 101. The swivel flange 100 is snapped into a length adjustment body 103. More particularly, the length adjustment body 103 includes a corresponding swivel flange 105 which traps the flange 100 of rotator body 98 while permitting relative rotation between the two bodies. Preferably, the two flanges 100 and 105 can be engaged by simply resiliently pressing the two bodies together. The length adjustment body 103 further includes a bore 104 to receive the fiber-optic bundle 20 therethrough and a threaded adjustment post 106 extending from its distal end. The threaded adjustment post 106 is adapted to engage an adjustment bore 110 of a catheter engagement body 108. Again, the engagement body 108 includes a bore 109 therethrough to receive the fiber-optic bundle 20. A mounting insert 111 is provided which fixes the tube 17 to the catheter engagement body 108. As shown in FIG. 2, the tube 17 mates with the tubing junction 31, which then mates with the delivery catheter 12. It should then thus be understood that any movement of the tube 17 is directly translated to an identically corresponding movement of delivery catheter 12. On the other hand, since the fiber-optic bundle 20 passes freely through certain components of the optic bundle adjustment means 21, any movement of the these components does not result in corresponding movement of the optical bundle 20.

In the use of the adjustment means 21, the fiber-optic bundle 20 is fastened to the locking base 94 by way of the locking nut 95 and resilient threaded post 96, as previously discussed. The relative position of the optic bundle 20 to the delivery catheter 12 can be adjusted by twisting the length adjustment body 103 relative to the catheter engagement body 108. When the adjustment post 106 is threaded more deeply into the adjustment bore 110 of catheter engagement body 108, the effective length or the catheter is shortened, while the fiber-optic bundle maintains its given length. Thus, the viewing end 73 of the bundle 20 moves closer to the open end 83 of the viewing tip 13. On the other hand, as the adjustment post 106 is threaded out of the bore 110, the effective length of the catheter is increased. With this motion, the viewing end 73 of the optical fiber bundle 20 effectively recedes within the viewing tip 13.

Once the bundle length has been set as required for the given procedure, the optical fiber bundle 20 can be rotated by twisting the rotator body 98 relative to the length adjustment body 103 and catheter engagement body 108. As the rotator body 98 is turned, the swivel flanges 100 and 105 cooperate so that no rotational movement is transmitted into the other components of the optical bundle adjustment means 21. The position and orientation of the viewing end 73 of the optical fiber bundle 20 can be verified radiographically by viewing the radio-opaque markings 115 at the end of the fiber-optic bundle 20. The ring 85 is formed of a radio-opaque material, such as stainless steel, or includes a radio-opaque marking similar to marking 115. Thus, the relative position of the bundle viewing end 73 to the open end 83 can be ascertained.

While the invention has been illustrated and described in detail in the drawings and foregoing description, the same is to be considered as illustrative and not restrictive in character, it being understood that only the preferred embodiment has been shown and described and that all changes mid modifications that come within the spirit of the invention are desired to be protected. For example, the catheter body 62 can include separate channels for irrigation fluid and for housing the fiber-optic bundle 20.

A modification to the deflection control mechanism 27 can eliminate the left stop body 49 and instead rely upon the right stop body 50 contacting the control sleeve 55 to limit the relative movement between the catheter 12 and deflection wire 57. By moving the pin 52 and right stop body 50 closer to the control sleeve movement of the catheter can be controlled with fewer components.

What is claimed is:

1. A system for direction visualization of the spinal epidural or intra-discal space comprising:
   a disposable flexible catheter sized for percutaneous introduction into the spinal space, said catheter having a proximal end and a distal end for insertion into the spinal space and including a first channel extending along the entire length of the catheter and a tip adjacent the distal end;
   a fiber-optic bundle sized to be removably slidably received within said first channel, said bundle having a proximal end and a distal end, and including imaging fibers and light fibers for connection to a camera and a light source, respectively;
   connection means at the proximal end of said catheter for connecting said fiber-optic bundle to the proximal end of said catheter and for adjustably positioning the distal end of said bundle relative to the distal end of said catheter;
   tip deflection means separate from said fiber-optic bundle for controllably defecting said tip of said catheter when the distal end is in the spinal space; and
   irrigation means for providing irrigation fluid through said catheter to the distal end of said catheter.

2. The system of claim 1, where said tip has a length dimension of less than about 2.5 cm measured from the distal end of said catheter.

3. The system of claim 1, wherein said catheter has an outer diameter of less than about 2.75 mm.

4. The system of claim 1, wherein said first channel is semi-circular.

5. The system of claim 1, further comprising radio-opaque means at the distal ends of said catheter mid fiber-optic bundle for permitting radiographic verification of the relative position of the distall end of said brindle to the distal end said catheter.

6. The system of claim 1, wherein said tip deflection means includes:
   a deflection wire having a first end and a second end and having a first portion adjacent said first end disposed outside said catheter and a second portion between said first portion and said second end extending throu gh said catheter;
   means for securing said second end of said deflection wire to said catheter at the distal end thereof;
   means for moving said catheter in a first direction from the proximal end toward the distal end of said catheter; and
   means for restraining said first end of said deflection wire against movement in said first direction as said catheter is moved in said first direction, whereby said deflection wire is placed in tension as it is pulled at its second end by said catheter to thereby cause said tip so deflect in the direction of said means for securing.

7. The system of claim 6, wherein said catheter includes a second channel and a slot opening into said second channel through which said second portion of said deflection wire extends.

8. The system of claim 6 wherein said means for moving includes means for limiting movement of said catheter in said first direction relative to said means for restraining to thereby control the amount of deflection of said tip.

9. The system of claim 8, wherein said means for limiting movement of said catheter in said first direction relative to said means for restraining is sufficient to deflect said tip between 0° and about 90°.

10. The system of claim 6, wherein said memos for moving said catheter includes means for rotating said catheter with the tip deflected, 11. The system of claim 6, wherein said means for restraining includes:
   an enlogated housing defining a cavity therein, said housing having openings at its ends for slidably receiving said catheter therethrough;
   a sleeve within said cavity and slidably disposed about said catheter;
   means for connecting said first end of said deflection wire to said sleeve; and
   said housing further defining a stop surface in said cavity for restraining movement of said sleeve in said first direction.

12. system of claim 11 wherein said means for moving includes means for limiting movement of said catheter in said first tirection relative to said means for restraining to thereby control the amount of deflection of said tip.

13. The system of claim 12, wherein said means for limiting movement includes:
   a first stop connected to said catheter and slidably disposed within said cavity; and
   a pin affixed to said housing and projecting into said cavity between said first stop and said sleeve, whereby said first stop contacts said pin when said catheter is moved in said first direction.

14. The system of claim 11, wherein initial contact between said sleeve and said stop surface defines a first position and initial contact between said first stop and said pin defines a second position so that displacement of said catheter between said first position and said second position will result in tip deflection of between 0° and about 90°.

15. The system of claim 13, wherein said means for limiting movement further includes a second stop connected to said catheter and slidably disposed within said cavity between said pin and said sleeve, whereby said second stop contacts said pin when said catheter is moved in a second direction opposite said first direction.

16. The system of claim 6, wherein said means for securing includes:
   a tube affixed at the distal end of said catheter and having an end opening beyond the distal end of said catheter; and second means for securing said second end of said deflection wire to said tube at said end opening.

17. The system of claim 16, wherein second means for securing includes a ring engaged to the interior of said tube at said end opening and beyound the distal end of said catheter said deflection wire being affixed to said ring.

18. The system of claim 16, wherein said catheter includes a second channel and a slot opening into said second channel through which said second portion of said deflection wire extends.

19. The system of claim 18, wherein said second channel terminates short of the distal end of the catheter and said catheter has a reduced outer dimension from the end of said second channel to the distal end of said catheter with said deflection wire extending from the end of said second channel adjacent the reduced outer dimension within said tube.

20. The system of claim 1, wherein said connection means includes:
    clamp means for clamping said fiber-optic bundle; and
    means for adjusting the length distance between the distal end of said catheter and said clamp means.

21. The system of claim 20, wherein said connection means further includes rotation means for rotating said fiber-optic bundle relative to said catheter.

22. A system for direct visualization of the spinal epidural or intra-discal space comprising:
    a disposable flexible catheter sized for percutaneous introduction into the spinal space, said catheter having an outer diameter of less than about 2.75 mm, said catheter having a proximal end and a distal end for insertion into the spinal space and including a first channel extending along the entire length of the catheter and a tip adjacent the distal end, wherein said first channel is semi-circular;
    a fiber-optic bundle sized to be removably slidably received within said first channel, said bundle having a proximal end and a distal end, and including imaging fibers and light fibers for connection to a camera and a light source, respectively;
    connection means at6 the proximal end of said catheter for connecting said fiber-optic bundle to the proximal end of said catheter and for adjustably positioning the distal end of said bundle relative to the distal end of said catheter;
    tip deflection means for controllably deflecting said tip of said catheter when the distal end is in the spinal space, wherein said tip has a length dimension of less than about 2.5 cm measured from the distal end of said catheter;
    radio-opaque means at the distal ends of said catheter and said fiber-optic bundle for permitting radiographic verification of the relative position of the distal end of said bundle to the distal end of said catheter; and
    irrigation means for providing irrigation fluid through said catheter to the distal end of said catheter, wherein said irrigation means includes said first channel in said catheter and means for fluidly connecting said first channel to a source of irrigation fluid, whereby irrigation fluid flows around said fiber-optic bundle when it is disposed within said first channel.

23. The system of claim 22, wherein:
said first channel is semi-circular having a radius, and said fiber-optic brindle has an outer diameter slightly less than the radius of said first channel.

24. A system for direct visualization of the spinal epidural or intra-discal space comprising:
    a disposable flexible catheter sized for percutaneous introduction into the spinal space, said catheter having a proximal end and a distal end for insertion into the spinal space and including a first channel extending along the entire length of the catheter and a tip adjacent the distal end;
    a fiber-optic bundle sized to be removably slidably received within said first channel, said bundle having a proximal end and a distal end, and including imaging fibers and light fibers for connection to a camera and a light source, respectively;
    connection means at the proximal end of said catheter for connecting said fiber-optic bundle to the proximal end of said catheter and for adjustably positioning t6he distal end of said bundle relative to the distal end of said catheter, wherein said connection means includes:
        clamp means for clamping said fiber-optic bundle; and
        means for adjusting the length distance between the distal end of said catheter and said clamp means, wherein said means for adjusting includes:
            a first housing attached to the proximal end of said catheter and defining a bore for slidably receiving said fiber-optici bundle therethrough,
            a second housing connected to said clamp means and defining a bore for receiving said fiber-optic bundle therethrough, and
            a threaded post on one of said first and second housing and a mating threaded bore defined in the other of said first and second housing, whereby said threaded post is adjustably threaded into said threaded bore to adjust the length distance between the distal end of said catheter and said clamp means; and
    tip deflection means for controllably deflecting said tip of said catheter when the distal end is in the spinal space.

25. The system of claim 24, wherein said connection means further includes rotation means for rotating said fiber-optic bundle relative to said catheter.

26. The system of claim 25, wherein said rotation means includes:
    a third housing attached to said clamp means and defining a bore for receiving said fiber-optic bundle therethrough; and
    means for rotatably mounting said third housing on said second housing to permit relative rotation between the housings.

27. An apparatus for controlling the viewing angle of an endoscope for direct visualization of the spinal epidural and intra-discal space, the endoscope being formed of a flexible catheter having a bendable tip and a fiber-optic bundle extending therethrough to the tip, the apparatus comprising:
    a deflection wire having a first end and a second end and having a first portion adjacent said first end disposed outside the catheter and a second portion between said first portion and said second end insertable through the catheter;
    means for securing said second end of said deflection wire to the catheter adjacent the tip thereof;

means for moving the catheter in a first direction from the proximal end toward the tip of the catheter, wherein said means for moving includes means for limiting movement of the catheter in said first direction relative to, said means for restraining to thereby control the amount of deflection of the tip; and means for restraining said first end of said deflection wire against movement in said first direction as the catheter is moved in said first direction, wherein said means for restraining includes:
 an elongated housing defin ing a cavity therein, said housing having openings at its ends for slidably receiving the catheter therethrough;
 a sleeve within said cavity and slidably disposed about the catheter;
 means for connecting said first end of said deflection wire to said sleeve; and
 said housing further defining a stop surface in said cavity for restraining movement of said sleeve in said first direction;
whereby said deflection wire is placed in tension as it is pulled at its second end by the catheter to thereby cause the tip to deflect in the direction of said means for securing.

28. The system of claim 27, wherein said means for limiting movement includes:
 a first stop connected to the catheter and slidably disposed within said cavity; and
 a pin affixed to said housing and projecting into said cavity between said first stop and said sleeve, whereby said first stop contacts said pin when the catheter is moved in said first direction.

29. The system of claim 28, wherein initial contact between said sleeve and said stop surface defines a first position and initial contact between said first stop and said pin defines a second position so that displacement of said catheter between said first position and said second position will result in tip deflection of between 0° and about 9°.

30. The system of claim 28, wherein said means for limiting movement further includes a second stop connected to the catheter and slidably disposed within said cavity between said pin and said sleeve, whereby said second stop contacts said pin when the catheter is moved in a direction opposite said first direction.

31. An endoscope for direect visualization of the spinal epidural and intra-discal space having a disposable component and a reusable optical component comprising:
 a flexible disposable catheter sized for percutaneous introduction into the spinal space, said catheter having a proximal end and a distal end for insertion into the spinal space and including a first channel extending along the entire length of the catheter;
 a fiber-optic bundle sized to be removably slidably received within said first channel, said bundle having a proximal end and a distal end, and including imaging fibers and light fibers for connection to a camera and a light source, respectively;
 connection means at the proximal end of said catheter for connecting said fiber-optic bundle to the proximal end of said catheter, for rotating said bundle relative to said catheter, and for adjustably positioning the distal end of said bundle relative to the distal end of said catheter, said connection means including;
 clamp means for clamping said fiber-optic bundle;
 rotation means for rotating said fiber-optic bundle relative to said catheter; and
 means for advancing and retracting the distal end of said catheter with respect to said clamp means; and
 irrigation means for providing irrigation fluid through said catheter to the distal end of said catheter.

32. The system of claim 32, wherein said means for advancing and retracting includes:
 a first housing attached to the, proximal end of said catheter and defining a bore for slidably receiving said fiber-optic bundle therethrough;
 a second housing connected to said clamp means and defining a bore for receiving said fiber-optic bundle therethrough; and
 a threaded post on one of said first and second housing and a mating threaded bore defined in the other of said first and second housing, whereby said threaded post is adjustably threaded into said threaded bore to adjust the length distance between the distal end of said catheter and said clamp means.

33. The system of claim 32, wherein said rotation means includes:
 a third housing attached to said clamp means and defining a bore for receiving said fiber-optici bundle therethrough; and
 means for rotatably mounting saiid third housing on said second housing to permit relative rotation between the housings.

34. A method for direct visualization of the spinal epidural and intra-discal space comprising the steps of:
 percutaneously inserting an endoscope formed of a flexible catheter with a fiber-optic bundle having both imaging and light fibers slidably disposed therein, the catheter having a deflectable tip unrelated to the fiber-optic bundle, and the fiber-optic bundle being connected to a light source and camera;
 advancing the catheter into the spinal space;
 keeping the fiber-optic bundle retracted within the catheter until the catheter tip reaches the region to be visualized;
 then extending the fiber-optic bundle relative to the catheter until the viewing end of the bundle is adjacent the end of the catheter; and
 radiographically verifying the position of the viewing end of the fiber-optic bundle relative to the end of the catheter.

35. A method for direct visualization of the spinal epidural and intra-discal space comprising the steps of:
 percutaneously inserting an endoscope formed of a flexible catheter with a fiber-optic bundle having both imaging and light fibers slidably disposed therein, the catheter having a deflectable tip unrelated to the fiber-optic bundle, and the fiber-optic bundle being connected to a light source and camera;
 advancing the catheter into the spinal space;
 keeping the fiber-optic bundleiretracted within the catheter until the catheter tip retches the region to be visualized;
 then extending the fiber-optic bundle relative to the catheter until the viewing end of he bundle is adjacent the end of the catheter;

radiographically verifying the position of the viewing end of the fiber-optic bundle relative to the end of the catheter; and rotating the fiber-optic bundle relative to the catheter to vary the view orientation through the viewing end of the fiber-optic bundle.

36. The method for direct visualization of the spine according to claim 34, further comprising the step of deflecting the catheter tip to vary the viewing angle of the viewing end of the fiber-optic bundle within the spinal space.

37. A method for direct visualization of the spinal epidural and intra-discal space comprising the steps of:

percutaneously inserting an endoscope formed of a flexible catheter with a fiber-optic bundle slidably disposed therein, the catheter having a deflectable tip and the fiber-optic bundle being connected to a light source and camera;

advancing the catheter into the spinal space;

keeping the fiber-optic bundle retracted within the catheter until the catheter tip reaches the region to be visualized;

then extending the fiber-optic bundle relative to the catheter until the viewing end of the bundle is adjacent the end of the catheter;

radiographically verifying the position of the viewing end of the fiber-optic bundle relative to the end of the catheter;

deflecting the catheter tip to vary the viewing angle of the viewing end of the fiber-optic bundle within the spinal space; and rotating the fiber-optic bundle relative to the catheter with the tip deflected to vary the view orientation through the viewing end of the fiber-optic bundle.

38. A method for direct visualization of the spinal epidural and intra-discal space comprising the steps of:

percutaneously inserting an endoscope formed of a flexible catheter with a fiber-optic bundle slidably disposed therein, the catheter having a deflectable tip and the fiber-optic bundle being connected to a light source and camera;

advancing the catheter into the spinal space;

keeping the fiber-optic bundle retracted within the catheter until the catheter tip reaches the region to be visualized;

then extending the fiber-optic bundle relative to the catheter until the viewing end of the bundle is adjacent the end of the catheter;

radiographically verifying the position of the viewing end of the fiber-optic bundle relative to the end of the catheter;

deflecting the catheter tip to vary the viewing angle of the viewing end of the fiber-optic bundle within the spinal space; and rotating the catheter within the spinal space with the tip deflected to further vary the viewing angle.

* * * * *